United States Patent [19]

Kallenbach et al.

[11] Patent Number: 5,288,685
[45] Date of Patent: Feb. 22, 1994

[54] ALKYLATION PROCESS AND CATALYST THEREFOR

[75] Inventors: Lyle R. Kallenbach; Roy F. Wright; David C. Miller, all of Bartlesville, Okla.

[73] Assignee: Phillips Petroleum Company, Bartlesville, Okla.

[21] Appl. No.: 35,334

[22] Filed: Mar. 19, 1993

Related U.S. Application Data

[62] Division of Ser. No. 973,493, Nov. 9, 1992, Pat. No. 5,233,199.

[51] Int. Cl.$^5$ .............................................. B01J 31/00
[52] U.S. Cl. ...................................... 502/168; 502/202
[58] Field of Search ................................. 502/168, 202

[56] References Cited

U.S. PATENT DOCUMENTS

| | | | |
|---|---|---|---|
| 3,044,954 | 7/1962 | Hirschler | 502/202 |
| 3,210,338 | 10/1965 | Huber et al. | 502/202 |
| 3,708,553 | 1/1973 | Olah | 585/730 |
| 3,887,635 | 6/1975 | Parker et al. | |
| 3,984,352 | 10/1976 | Rodewald | |
| 4,065,516 | 12/1977 | Moser, Jr. et al. | 585/730 |
| 4,094,922 | 6/1978 | Bartek et al. | |
| 4,613,723 | 9/1986 | Olah | 585/730 |
| 5,220,095 | 6/1993 | Hommeltoft et al. | 585/720 |

FOREIGN PATENT DOCUMENTS

0433954A1 1/1991 European Pat. Off. .
2017521A 10/1979 United Kingdom .

Primary Examiner—Patrick P. Garvin
Assistant Examiner—E. D. Irzinski
Attorney, Agent, or Firm—K. K. Brandes

[57] ABSTRACT

A composition of matter comprises trifluoromethanesulfonic acid on a solid support material which contains boron phosphate and/or boron sulfate. Preferred support materials are boron phosphate, boron phosphate-coated silica and boron sulfate-coated silica. The above composition is used as a catalyst for alkylating at least one $C_2$-$C_7$ alkane (preferably isobutane or an isopentane) with at least one $C_2$-$C_7$ alkene (preferably butene-2).

20 Claims, No Drawings

ALKYLATION PROCESS AND CATALYST THEREFOR

This application is a division of Ser. No. 07/973,493, filed Nov. 9, 1992 and now U.S. Pat. No. 5,233,199.

BACKGROUND OF THE INVENTION

In one aspect, this invention relates to a novel composition of matter, which is effective as an alkylation catalyst, comprising trifluoromethanesulfonic acid and an inorganic solid support material. In another aspect, this invention relates to the alkylation of alkanes (paraffins) with alkenes (monoolefins), in the presence of a novel solid catalyst composition comprising trifluoromethanesulfonic acid and a solid support material.

The use of supported trifluoromethanesulfonic acid catalyst for the alkylation of alkanes with alkenes is known and has been described in the patent literature (e.g., in European Patent Application having Publication No. EP 0 433 954 A1). The present invention is directed to a novel, effective alkylation catalyst composition comprising trifluoromethanesulfonic acid and specific inorganic support materials, and to the use of said catalyst composition in an alkylation process.

SUMMARY OF THE INVENTION

It is an object of this invention to provide a novel solid composition of matter which is active as an alkylation catalyst. It is another object of this invention to alkylate alkanes with alkenes in the presence of a novel solid catalyst comprising trifluoromethanesulfonic acid and an inorganic support material. Other objects and advantages will be apparent from the detailed description of the appended claims.

In accordance with this invention, a composition of matter (effective as a catalyst for alkylating alkanes with alkenes) comprises trifluoromethanesulfonic acid and a solid support material comprising at least one boron compound selected from the group consisting of boron phosphate and boron sulfate. Preferably, this composition of matter consists essentially of trifluoromethanesulfonic acid and boron phosphate. In another preferred embodiment, the composition of matter of this invention consists essentially of trifluoromethanesulfonic acid and boron phosphate-coated silica. In a further preferred embodiment, the composition of this invention consists essentially of trifluoromethanesulfonic acid and boron sulfate-coated silica.

Also in accordance with this invention, a process for alkylating alkanes comprises the step of contacting at least one feed alkane (i.e., at least one straight-chain alkane or at least one branched alkane or a mixture thereof) containing about 2-7 carbon atoms per molecule with at least one feed alkene (i.e., at least one straight chain alkene or at least one branched alkene or a mixture thereof) containing about 2-7 carbon atoms per molecule with the above-described catalyst composition comprising trifluoromethanesulfonic acid and at least one solid support material comprising boron phosphate and/or sulfate, at effective alkylation conditions so as to obtain at least one product alkane containing at least two more carbon atoms per molecule than said at least one feed alkane.

DETAILED DESCRIPTION OF THE INVENTION

The composition of matter of this invention comprises $CF_3SO_3H$ on an inorganic support material which contains $BPO_4$ and/or $B_2(SO_4)_3$. Generally, the support material contains about 20 to about 100 weight-% $BPO_4$ and/or $B_2(SO_4)_3$ and up to about 80 weight-% (preferably about 0.5-80 weight-%) $SiO_2$. Other inorganic solids, such as alumina and activated carbon, may be used in lieu of or in addition to silica. The BET/$N_2$ surface area of these support materials generally is in the range of about 200 to about 400 $m^2/g$. Preferably, the particles of the composition of matter have a size in the range of smaller than 20 mesh and larger than 40 mesh.

The composition of matter of this invention can be prepared in any suitable manner. Preferably, the $BPO_4$-containing support material is prepared by the reaction of a boric acid ester $B(OR)_3$ wherein each R can be independently selected from alkyl radicals containing 1-5 carbon atoms (more preferably tri-n-propyl borate) and orthophosphoric acid ($H_3PO_4$), with $SiO_2$ either being absent during this reaction (so as to prepare a 100% $BPO_4$ material) or $SiO_2$ being present during this reaction in an amount as to provide a material containing up to about 80 weight-% $SiO_2$ (preferably about 0.5-80 weight-% $SiO_2$). When a $B_2(SO_4)_3$-containing support material is used, it is preferably prepared by the reaction of a boric acid ester (such as tri-n-propyl borate) and sulfuric acid, either in the absence of or in the presence of up to 80 weight-% $SiO_2$ (preferably about 0.5-80 weight-% $SiO_2$). The thus-obtained support material is then preferably calcined (generally for about 2-5 hours at a temperature of about 250°-500° C., either in air or in a $N_2$ atmosphere). The $CF_3SO_3H$ catalyst component can be applied to the support material in any suitable manner. Generally, it is added in liquid form to the top layer of the solid support material (preferably being present in a catalyst bed) just prior to the alkylation reaction, generally at a weight ratio of $CF_3SO_3H$ to said support material in the range of about 0.02:1 to about 0.4:1.

The solid compositions or matter described above are employed as catalysts in the alkylation process of this invention. The process for alkylating $C_2$-$C_7$ alkanes (preferably isoalkanes, i.e., branched alkanes) with $C_2$-$C_7$ alkenes (preferably those containing an internal double bond) can be carried out in any suitable manner. The contacting of a mixture of at least one feed alkane and at least one feed alkene, generally at a molar alkane-/alkene ratio of about 6:1 to about 12:1 (preferably about 8:1 to about 10:1), with one of the above-described catalyst compositions can be carried out at effective alkylation conditions, preferably at a relatively low temperature of up to about 100° C., preferably about −10° to about 100° C., more preferably about 0°-30° C., most preferably about 0°-5° C., preferably at a pressure of about 2-6 atm.

The alkane/alkene feed mixture can be contacted with the catalyst composition in any suitable mode, preferably in a fixed catalyst bed operation in which the feed mixture flows downward through a solid catalyst layer, generally at a liquid hourly space velocity of about 0.5-5 (preferably about 1-3) $cm^3$ alkane/alkene feed per $cm^3$ catalyst composition per hour. The alkylation process can be carried out in a continuous manner or as a batch process. Generally, the $CF_3SO_3H$ component moves as a zone along the solid catalyst bed in the direction of the alkylation feed. When the $CF_3SO_3H$ zone approaches the exit region of the catalyst bed, the reactant flow can be reversed (so that the $CF_3SO_3H$ zone can travel back through the catalyst bed).

Suitable feed alkanes are normal (straight chain) alkanes and isoalkanes (i.e., branched) alkanes, each containing 2–7 carbon atoms per molecule. Non-limiting examples of suitable alkanes are propane, n-butane, isobutane, n-pentane, isopentanes (2-methylbutane and 2,2-dimethylpropane), n-hexane, isohexanes (such as 2-methylpentane, 3-methylpentane, 2,2-dimethylbutane), n-heptane and isoheptanes (such as methyl-substituted hexanes and dimethyl-substituted pentanes). Presently preferred are $C_3$–$C_6$ alkanes, more preferably branched $C_4$–$C_6$ alkanes. Particularly preferred feed alkanes are isobutane and 2-methylbutane.

Suitable feed alkenes are normal (straight chain) and branched alkenes containing one C=C double bond and 2–7 carbon atoms per molecule, preferably those containing an internal C=C double bond (more preferably in the 2 position). Non-limiting examples of suitable alkenes are propylene, butene-1, butene-2, isobutylene, pentene-1, pentene-2, isopentenes, hexene-1, hexene-2, hexene-3 and isohexenes. Preferred alkenes are those containing 3–5 carbon atoms per molecule. The presently more preferred feed alkene is butene-2.

The alkylation process of this invention generally generates a multitude of hydrocarbon products containing a greater number of carbon atoms per molecule than the feed alkane(s), as is demonstrated in the examples. Thus, it is generally necessary to separate the various formed hydrocarbon products from one another and from unconverted feed hydrocarbons. This separation can be carried out in any suitable manner, generally by fractional distillation (possibly in the presence of an extractant, i.e., by extractive distillation), as can be determined by persons skilled in the various liquid-liquid separation technologies.

The following examples are provided to further illustrate the processes of this invention, and are not to be construed as unduly limiting the scope of this invention.

EXAMPLE I

This example illustrates the preparation of several solid boron-containing catalyst support materials.

Boron phosphate ($BPO_4$) was prepared by adding, with stirring over a period of about 3 hours, 93.22 grams of tri-n-propyl borate (normal boiling point: 175°–177° C.; obtained from Aldrich Chemical Company, Milwaukee, Wis.) to 54.82 grams of a aqueous phosphoric acid (containing about 85 weight-% $H_3PO_4$ and 15 weight-% $H_2O$) in a 3-neck flask, at about 80° C. under a nitrogen gas atmosphere. The reaction mixture was heated under reflux conditions to a temperature of about 120° C. Thereafter, essentially all liquids (mainly water and formed propanol) were distilled off. The white solid residue of $BPO_4$ was vacuum-dried at a temperature of about 120° C. for 3 hours. 25.5 grams of dry boron phosphate (B:P atomic ratio 1.04:1) was obtained.

$BPO_4/SiO_2$ A, containing 27 weight-% $BPO_4$, was prepared as follows. 34.35 grams of calcined 20-40 mesh silica ($BET/N_2$ surface area:347 $m^2/g$; obtained from Davison Chemical Division of W. R. Grace and Co., Baltimore, Md.) and 13.8 grams of a mixture of 85 weight-% $H_3PO_4$ and 15 weight-% $H_2O$ were placed into a 3 neck glass flask. The mixture was heated to about 80° C. under a $N_2$ atmosphere, and 22.70 g tri-n-propyl borate was added dropwise, with stirring, to the above mixture. The entire reaction mixture was heated for 2 hours under reflux conditions. Thereafter, essentially all liquids (mainly propanol and water) were distilled off at a temperature of about 120° C. The solid residue was dried for 3 hours at a temperature of about 150° C. under vacuum conditions. 48.05 g of dry $BPO_4$ on $SiO_2$ (containing 27 weight-% $BPO_4$) was obtained.

$BPO_4/SiO_2$ B, containing 75 weight-% $BPO_4$, was prepared essentially in accordance with the above-described procedure for $BPO_4/SiO_2$ A, except that the amount of added silica was adjusted to about 25 weight-% $SiO_2$ of the support material (in lieu of 73 weight-% of $SiO_2$ used in $BPO_4/SiO_2$ A) and that $BPO_4/SiO_2$ B had been heated for 2 hours at 300° C. in air.

$B_2(SO_4)_3/SiO_2$ A, containing 35 weight-% $B_2(SO_4)_3$, was prepared as follows. 22.70 grams of (0.121 mole) of tri-n-propyl borate, 17.76 grams of 100% $H_2SO_4$ and 34.35 grams of silica (described in Example I were mixed and heated, with stirring, for about 2 hours at 80° C. Thereafter, the reaction mixture was heated to 120° C., and liquids (mainly formed propanol) were distilled off. The dry pink solid residue was calcined in air at 275° C. for 2 hours.

$B_2(SO_4)_3/SiO_2$ B, containing 70 weight-% $B_2(SO_4)_3$, was prepared essentially as described above for $B_2(SO_4)_3/SiO_2$ A, except that the weight of silica was adjusted to provide 30 weight-% of $SiO_2$ in the finished catalyst (in lieu of 65 weight-% $SiO_2$).

EXAMPLE II

This example illustrates the use of the catalysts comprising trifluoromethanesulfonic acid and the solid support materials described in Example I.

Each of the five materials described in Example I and silica (as control support material) were ground and sieved. Particles having a mesh size of smaller than 20 but larger than 40 were calcined at about 500° C. for about 2–2½ hours. A U-shaped stainless steel reactor tube (inner diameter: 0.29 inch; length: 60 inches) was filled with one of the above materials. About 6.6 grams (3.9 $cm^3$) of trifluoromethanesulfonic acid was then added to the top (entrance) zone of the packed column. The entire column was maintained at a temperature of about 0° C., and a liquid alkylation feed of 10 weight-% butene-2 (containing approximately equal amounts of cis and trans isomers) and 90 weight-% isobutane were pumped through the packed column at a rate of 1 $cm^3$ per minute. The exiting alkylation product was analyzed about every 60 minutes by means of a gas chromatograph. Each test lasted about 50–60 hours. Average test results are summarized in Table I.

TABLE I

| Catalyst | % Olefin Conversion | Alkylate Product Composition | | | | | Alkylate Octane No.[6] |
| --- | --- | --- | --- | --- | --- | --- | --- |
| | | C5 | C6 | C7 | C8 | C9+ | |
| $CF_3SO_3H$ on $SiO_2$[1] | 99.6 | 14.5 | 6.2 | 5.4 | 54.8 | 9.9 | 92.8 |
| $CF_3SO_3H$ on $BPO_4$ | 98.5 | 10.3 | 4.4 | 4.4 | 70.7 | 5.0 | 94.6 |

TABLE I-continued

| Catalyst | % Olefin Conversion | Alkylate Product Composition | | | | | Alkylate Octane No.[6] |
|---|---|---|---|---|---|---|---|
| | | C5 | C6 | C7 | C8 | C9+ | |
| CF$_3$SO$_3$H on BPO$_4$/SiO$_2$ A[2] | 97.8 | 15.5 | 5.9 | 5.0 | 60.4 | 6.1 | 93.3 |
| CF$_3$SO$_3$H on BPO$_4$/SiO$_2$ B[3] | 99.4 | 11.3 | 5.4 | 5.5 | 62.1 | 10.0 | 92.8 |
| CF$_3$SO$_3$H on B$_2$(SO$_4$)$_3$/SiO$_2$A[4] | 100 | 4.6 | 3.7 | 4.5 | 71.2 | 14.4 | 93.6 |
| CF$_3$SO$_3$H on B$_2$(SO$_4$)/SiO$_2$B[5] | 99.8 | 12.0 | 5.4 | 5.4 | 61.8 | 6.0 | 92.9 |

[1]BET/N$_2$ surface area: about 347 m$^2$/g (described in Example I)
[2]containing 27 weight-% BPO$_4$
[3]containing 75 weight-% BPO$_4$
[4]containing 35 weight-% B$_2$(SO$_4$)$_3$
[5]containing 70 weight-% B$_2$(SO$_4$)$_3$
[6](research octane number + motor octane number) divided by 2

Test data in Table I clearly show that the amount of desirable C$_8$ hydrocarbon products was greatest in runs employing BPO$_4$-containing and B$_2$(SO$_4$)$_3$-containing catalyst support materials. The octane numbers of the alkylates produced in runs employing BPO$_4$-containing and B$_2$(SO$_4$)$_3$-containing catalyst support materials were generally higher than the octane number of the alkylate obtained in the CF$_3$SO$_3$H/SiO$_2$ run. An additional alkylation test (not described in detail herein) was carried out with a 2-methylbutane/butene-2 feed in the presence of a CF$_3$SO$_3$H/BPO$_4$/SiO$_2$ catalyst, at substantially the same reaction conditions as those described above.

Reasonable variations, modifications and adaptations for various usages and conditions can be made within the scope of the disclosure and the appended claims, without departing from the scope of this invention. Also, it is expected that the catalyst materials of this invention will be active as catalysts for isomerizing alkanes (in particular C$_5$-C$_8$ straight-chain and branched alkanes) and cycloalkanes (in particular methylcyclopentane, which will be isomerized to cyclohexane).

That which is claimed is:

1. A composition of matter comprising trifluoromethanesulfonic acid and a solid material comprising boron phosphate, wherein the weight ratio of trifluoromethanesulfonic acid to said solid material is in the range of about 0.02:1 to about 0.4:1.

2. A composition of matter in accordance with claim 1, wherein said solid material consists essentially of boron phosphate.

3. A composition of matter in accordance with claim 1 consisting essentially of trifluoromethanesulfonic acid and boron phosphate.

4. A composition of matter in accordance with claim 1, wherein said solid material consists essentially of boron phosphate and about 0.5-80 weight-% silica.

5. A composition of matter in accordance with claim 4, wherein said support material has been prepared by the reaction of tri-n-propyl borate and orthophosphoric acid in the presence of silica.

6. A composition of matter in accordance with claim 4 consisting essentially of trifluoromethanesulfonic acid and boron phosphate-coated silica.

7. A composition of matter in accordance with claim 1, wherein said solid material comprises about 20-100 weight-% boron phosphate.

8. A composition of matter comprising trifluoromethanesulfonic acid and a solid material comprising boron sulfate, wherein the weight ratio of trifluoromethanesulfonic acid to said solid material is in the range of about 0.02:1 to about 0.4:1.

9. A composition of matter in accordance with claim 8, wherein said solid material consists essentially of boron sulfate.

10. A composition of matter in accordance with claim 8 consisting essentially of trifluoromethanesulfonic acid and boron sulfate.

11. A composition of matter in accordance with claim 8, wherein said solid material consists essentially of boron sulfate and about 0.5-80 weight-% silica.

12. A composition of matter in accordance with claim 11, wherein said solid material has been prepared by the reaction of tri-n-propyl borate and sulfuric acid in the presence of silica.

13. A composition of matter in accordance with claim 11 consisting essentially of trifluoromethanesulfonic acid and boron sulfate-coated silica.

14. A composition in accordance with claim 8, wherein said solid material comprises about 20-100 weight-% boron sulfate.

15. A composition of matter comprising trifluoromethanesulfonic acid and a solid material comprising boron phosphate and boron sulfate, wherein the weight ratio of trifluoromethanesulfonic acid to said solid material is in the range of about 0.02:1 to about 0.4:1.

16. A composition in accordance with claim 15, wherein said solid material consists essentially of boron phosphate and boron sulfate.

17. A composition in accordance with claim 15 consisting essentially or trifluoromethane sulfonic acid, boron phosphate and boron sulfate.

18. A composition in accordance with claim 15, wherein said solid material consists essentially of boron phosphate, boron sulfate and about 0.5-80 weight-% silica.

19. A composition in accordance with claim 18 consisting essentially of trifluoromethanesulfonic acid, boron phosphate, boron sulfate and silica.

20. A composition in accordance with claim 15, wherein the combined weight percentage of boron phosphate and boron sulfate in said solid material is about 20-100.

* * * * *